United States Patent [19]

Zackheim et al.

[11] Patent Number: 4,764,520
[45] Date of Patent: Aug. 16, 1988

[54] AGENTS FOR THE TREATMENT OF LEUKEMIA

[76] Inventors: Herschel S. Zackheim, 133 Arch St., Redwood City, Calif. 94062; Davide R. Grassetti, 26 Northgate Ave., Berkeley, Calif. 94708

[21] Appl. No.: 42,480

[22] Filed: Apr. 24, 1987

[51] Int. Cl.$^4$ .............................................. A61K 31/44
[52] U.S. Cl. ................................................... 514/350
[58] Field of Search .......................................... 514/350

[56] References Cited

U.S. PATENT DOCUMENTS 4,521,425  6/1985  Grassetti ............................ 514/350

Primary Examiner—Jerome D. Goldberg

[57] ABSTRACT

This invention relates to a method for preventing the occurrence of leukemia in mammals. Alternately, in mammals affected with leukemia, the course of the disease is delayed and life expectancy and well-being are increased. This is achieved by administration of 6-mercaptonicotinic acid or its alkali metal salts.

3 Claims, No Drawings

AGENTS FOR THE TREATMENT OF LEUKEMIA

AGENTS FOR THE PREVENTION AND TREATMENT OF LEUKEMIA

It has been discovered that administration of appropriate doses of 6-mercaptonicotinic acid (6MNA) to leukemia bearing mammals delays the course of the disease. Alternately, if healthy mammals are exposed to conditions which would induce leukemia (e.g. inoculation of leukemia cells), the onset of the disease is often prevented by 6MNA. No adverse effects have been observed due to administration of this compound or its salts.

6MNA was administered orally, admixed with the chow, to BDF1 mice, males or females, of weight between 18 and 25 grams. These mice were inoculated with $10^5$ cells of L1210 leukemia, from a culture, suspended in 0.1 to 0.5 ml of physiological buffer. The injection was done intraperitoneally. The test mice received a diet containing 6MNA, beginning 2 to 3 days before inoculation of the L1210 cells. The mice were examined daily, and the extent of the tumor, if any, was assessed.

EXAMPLE 1.

Two groups of 6 mice each were inoculated with L1210 leukemia cells intraperitoneally. One group was fed regular mouse chow (control). The second group received a chow containing 1% by weight of 6MNA. Access to the chow was allowed ad libitum. The number of survivors after 30 days in each group is listed in the following Table:

|  | 30-day Survivors |
|---|---|
| Group I (control) | 0/6 |
| Group II (1% 6MNA) | 2/6 |

The survivors had a low grade leukemia.

EXAMPLE 2

This trial was performed as described in Example I, except for the concentration of 6MNA.

|  | 30-day Survivors |
|---|---|
| Group I (control) | 0/11 |
| Group II (2% 6MNA) | 4/11 |

One mouse of group II was free of tumor, the other survivors had a low grade leukemia.

The examples show that administration of 6MNA increased the number of 30-day survivors. In addition it was found that when 2% 6MNA was administered, some of the mice had no evidence of tumor, at a time when all the controls were dead. It should also be noted that in the 6MNA groups the surviving mice had usually a low grade leukemia.

This shows that 6MNA decreases the incidence of "takes" when leukemia cells are injected into mice, and that if any tumors develop in these mice, they usually grow at a substantially slower rate that in the control animals.

6MNA is therefore useful (a) as a preventive agent when mammals are exposed to conditions causing the onset of leukemia; (b) as retardant of the development of leukemia when the mammals are affected with that disease.

This signifies that administration of 6MNA to individuals exposed to carcinogenic stimuli (e.g. radiation, chemicals) which usually would bring about leukemia, decreases the likelihood of their acquiring this malignant disease. Alternately, administration of 6MNA to individuals affected with leukemia will lessen the severity of the disease, and give them a longer life expectancy, either free of the disease, or with an improved quality of life.

6MNA can be administered orally or parenterally, also as the aqueous solution of its alkali metal salts.

We claim:

1. The method of treating mammals affected with leukemia so as to delay or arrest the course of the disease, which comprises administering to said mammals an amount of 6-mercaptonicotinic acid, or an alkali metal salt thereof, effective to bring about this delay or arrest of leukemia.

2. The method of claim 1 wherein the amount of 6-mercaptonicotinic acid or an alkali metal salt thereof is administered in the range about 20 milligrams to about 5 grams daily.

3. The method of treating mammals affected with leukemia so as to delay or arrest the course of the disease, which comprises administering to said mammals 6-mercaptonicotinic acid, or its alkali metal salts, in amounts sufficient to maintain a range of $10^{-9}$ to $10^{-3}$ molar in the body of the mammal.

* * * * *